United States Patent [19]

Cannon et al.

[11] 4,346,606

[45] Aug. 31, 1982

[54] RATE METER

[75] Inventors: Raymond E. Cannon, San Diego; Jon A. Jenkins, Rancho Santa Fe; Larry L. Wilson, Poway, all of Calif.

[73] Assignee: IMED Corporation, San Diego, Calif.

[21] Appl. No.: 128,662

[22] Filed: Mar. 10, 1980

[51] Int. Cl.³ .................... G01F 13/00; A61M 5/16
[52] U.S. Cl. ........................ 73/861.41; 128/214 E; 128/DIG. 13
[58] Field of Search .......... 73/861.41, 861.05, 861.77, 73/861.72; 128/214 E, DIG. 13; 340/609

[56] References Cited

U.S. PATENT DOCUMENTS

3,390,577  7/1968  Phelps et al. ..................... 73/861.41
3,545,271  12/1970  Amir et al. ....................... 73/861.41
4,038,982  8/1977  Burke et al. ..................... 128/214 E

FOREIGN PATENT DOCUMENTS

2236518  2/1975  France ............................. 73/861.41

*Primary Examiner*—Charles A. Ruehl
*Attorney, Agent, or Firm*—Ellsworth R. Roston; Charles H. Schwartz

[57] ABSTRACT

A rate meter senses successive drops of fluid flowing through a conduit and produces gating periods with time durations corresponding to the period of time between such successive drops. The rate meter then determines the number of incremental time periods in each gating period. The rate meter generates the reciprocal of this determination to obtain an indication of the rate of fluid flow. The rate meter may be self-contained. It includes a housing having a vertically disposed channel constructed to retain the conduit and a horizontally disposed channel communicating with the vertically disposed channel. The horizontally disposed channel is constructed to receive a cross bar made from a resilient material and fixedly disposed on the conduit. The cross bar supports the rate meter in a freestanding relationship. The cross bar may be provided with slots near its ends to enhance its resiliency. The cross bar may also be provided with detents at its ends to cooperate with detents at the ends of the horizontally disposed channel on the rate meter to retain the rate meter on the cross bar. The vertically disposed channel in the rate meter may be defined by first and second oppositely disposed walls in the housing. A light source may be disposed in the first wall and a light sensor may be disposed in the second wall. Visual indicating means may be disposed on a front wall of the housing to provide a numerical indication of the rate of fluid flow.

24 Claims, 6 Drawing Figures

RATE METER

This invention relates to a rate meter for indicating the rate at which drops of fluid fall through a conduit. More particularly, the invention relates to a meter which indicates instantaneously the actual rate of drop generation without any averaging of such rate as in the prior art. The invention further relates to a self-contained rate meter which is constructed to be carried manually by a hospital attendant and to be disposed in fixed position on the conduit for instantaneously indicating the rate of fluid flow.

As the practice of medicine becomes increasingly sophisticated, it becomes increasingly evident that medicines have to be introduced to a patient at particular rates to have optimal benefits. Furthermore, the rate of introduction is dependent upon a number of factors including the age, sex, weight and physical condition of a patient. For example, as a patient recuperates from an operation, individual medicines have to be introduced at variable rates to the patient. This is particularly true when fluids are introduced on an intravenous basis to the patient.

Apparatus is now in use for measuring the rate at which intravenous fluid is introduced to a patient. Such apparatus has severe disadvantages. The apparatus counts a number of successive drops and averages the time between such successive drops to determine the rate of fluid flow. This average may not be reliable since the actual rate may vary considerably during the period between the first and last drops in the averaging period. Furthermore, the time required to determine this average is time consuming, particularly to a hospital attendant such as a nurse who has a number of other duties to perform.

There are other problems with the rate meters now in use. For example, the rate meters are not self-contained. This has required the hospital attendant to waste precious time in locating a rate meter and in coupling the rate meter to the conduit in order to obtain a rate indication. Furthermore, the arrangement for coupling the rate meter to the conduit has been awkward.

A considerable effort has been made to provide a rate meter which overcomes the above difficulties. Such efforts have been far from successful. The rate meters now in use are still unreliable, time-consuming and awkward. The problem has been so long standing, and the solution so elusive, that hospital attendants have accepted the disadvantages in the rate meters now in use as inevitable. Actually, a number of hospital attendants even count drops visually and measure the time between drops with a watch.

This invention provides a rate meter which overcomes the above disadvantages. The rate meter provides an instantaneous and reliable indication of the rate of fluid flow. The rate meter is self-contained so that it can be retained in the pocket or on the belt of a hospital attendant and carried by that attendant from one patient to the next. The rate meter is easily coupled to the conduit introducing medicinal fluid to a patient and can be easily decoupled from the conduit after an indication of the actual rate of fluid flow through the conduit has been obtained.

In one embodiment of the invention, apparatus is provided for indicating the rate at which drops of fluid flow from a source 10 through a drip chamber 12 to a patient 14. A schematic diagram of the electrical circuitry in such a rate meter is shown in FIG. 1.

Figure 1:
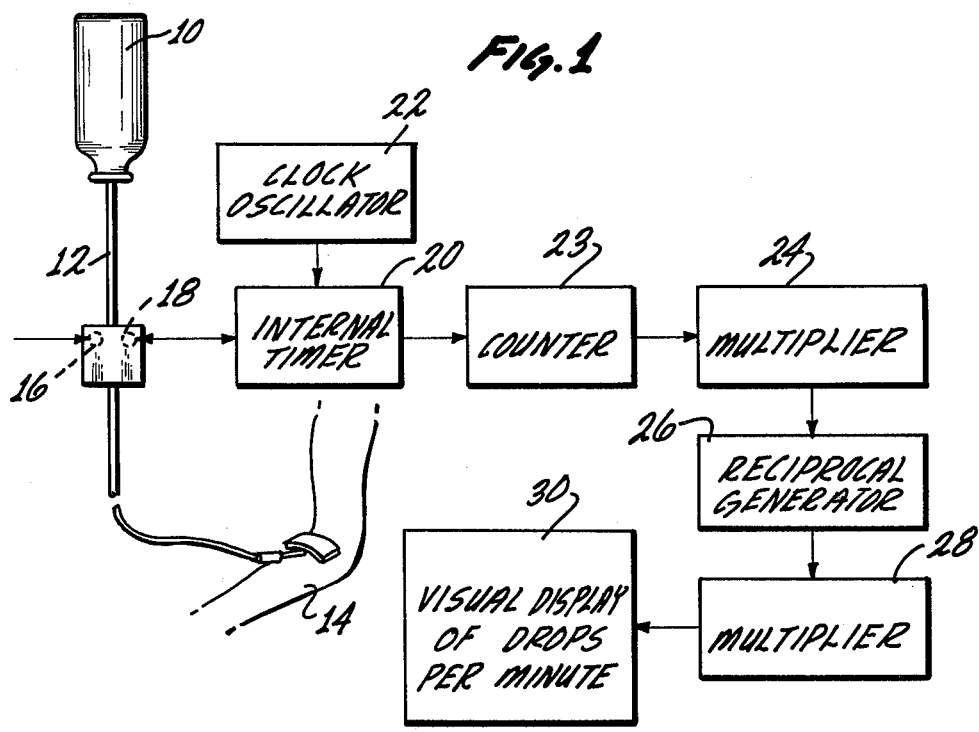
FIG. 1 is a block diagram schematically illustrating the electrical circuitry in a rate meter constituting one embodiment of the invention.
Figure 2:
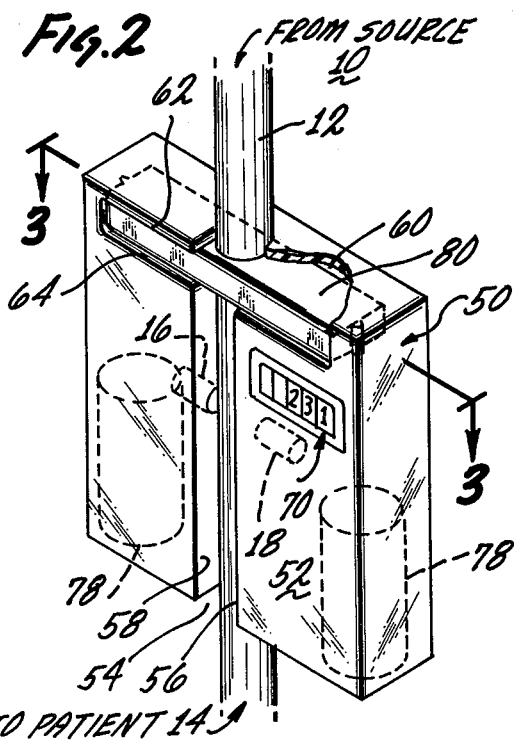
FIG. 2 is a perspective view of the rate meter shown in FIG. 1 when the rate meter is disposed on a drip chamber to indicate the rate at which drops of a fluid flow through the conduit.

The electrical circuitry shown in FIG. 1 includes a light source 16 which is disposed on one side of the drip chamber 12. It also includes a light sensor 18 which is disposed on the opposite side of the drip chamber 12. When no fluid flows through the drip chamber 12 past the light source 16 and the sensor 18, the light from the source 16 passes to the sensor 18 and produces a voltage at the sensor. However, when a drop of fluid passes through the conduit 12 at a position between the source 16 and the sensor 18, it scatters the light passing to the sensor and causes the sensor to produce a signal.

The signals from the sensor 18 are introduced to an internal timer 20 which is constructed to serve as a gate. The timer 20 also receives signals from an oscillator 22 which provides clock signals at a precisely controlled frequency. The signals passing through the timer 20 are introduced to a counter 23, the output of which passes to a multiplier 24. The output signals from the multiplier 24 are in turn introduced to a reciprocal generator 26, the output of which is connected to a multiplier 28. The output from the multiplier passes to a visual display 30.

Each pulse from the sensor 18 triggers the timer 20 to provide for the passage of signals from the oscillator 22 through the timer until the production of the next signal by the sensor 18. As a practical matter, the timer 20 serves as a gate for passing the clock signals from the oscillator 22 to the counter 23. This causes each count in the counter 23 to represent the total number of clock signals produced between successive pairs of signals from the sensor 18.

When the oscillator 22 produces signals at a particular frequency such as one (1) per second, the multiplier 24 may be omitted. However, the signals from the oscillator 22 may occur at a different rate. For example, the signals from the oscillator 22 may occur every 0.0016 seconds. Under such circumstances, the multiplier 24 may multiply the count in the counter 23 by 0.0016 to indicate the period between each successive pair of signals from the sensor 18.

The rate is determined by obtaining the reciprocal of the numerical value produced by the multiplier 24. This is accomplished in the generator 26, which accordingly indicates the rate of drops per second. Conversion to a rate per minute may be obtained in the multiplier 28 by multiplying by a factor of sixty (60) the value in the generator 26. The value obtained by the multiplier 28 may be indicated by decimal numbers in the visual display 30.

The rate meter described above has certain important advantages. It provides an instantaneous display of the current rate of drops of fluid by measuring the time between the last two drops and operating upon this measurement. In this way, a hospital attendant such as a nurse is able to obtain reliable indications of rate rather than imprecise measurements such as often occur when a rate is determined by averaging the number of drops over a preselected period of time. Furthermore, the determination of rate from two successive drops of fluid is considerably faster than the averaging of the number of drops over a preselected period of time. This is particularly important to hospital attendants who may have to make a round of calls to different patients under harried circumstances.

The rate meter described above may be self-contained. The meter may be easily coupled to the drip chamber 12 to obtain rate indication and may be easily uncoupled from the drip chamber 12 after such determinations. For example, the rate meter may be disposed in a housing generally indicated at 50. The housing 50 may be easily molded from a suitable material such as a plastic. The housing 50 may include a front panel 52 having a vertically disposed channel 54 defined by oppositely disposed side walls 56 and 58. The light source 16 may be disposed in the wall 58 and the sensor 18 may be disposed in the wall 56 at substantially the same vertical level as the source 16.

Figure 3:
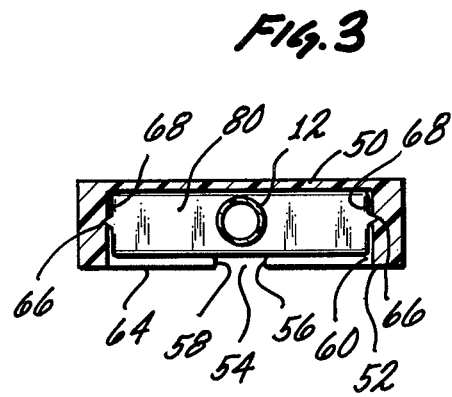
FIG. 3 is a sectional view of the rate meter and is taken substantially on the line 3—3 of FIG. 2.

A horizontally disposed channel 60 communicates with the vertically disposed channel 54. Preferably the channel 60 is disposed above the channel 54 at a position which causes the channels 60 and 54 to define a T-shaped configuration. The channel 60 is defined by an upper ledge 62 and by a lower support wall 64. Detents such as recesses 66 (FIG. 3) are disposed in vertical walls 68 at the ends of the horizontally disposed channel 60.

The circuitry shown in FIG. 1 and described above may be packaged in the housing 50. The circuitry may include batteries 78 disposed preferably in the columns which are defined by the vertically disposed side walls 56 and 58. The circuitry is connected to the display 30 disposed on the front panel 52 to provide a visual display such as in decimal form.

A coupling member generally indicated at 80 is fixedly disposed on the drip chamber 12. The coupling member 80 is constructed to be disposed in the horizontally disposed channel 60 to support the housing 50 on the drip chamber 12. When this occurs, the drip chamber 12 is positioned in the vertically disposed channel 54 between the light source 16 and the sensor 18. As a result, the rate meter is in position to provide an indication of the rate at which drops of fluid may be falling through the drip chamber.

Figure 4:
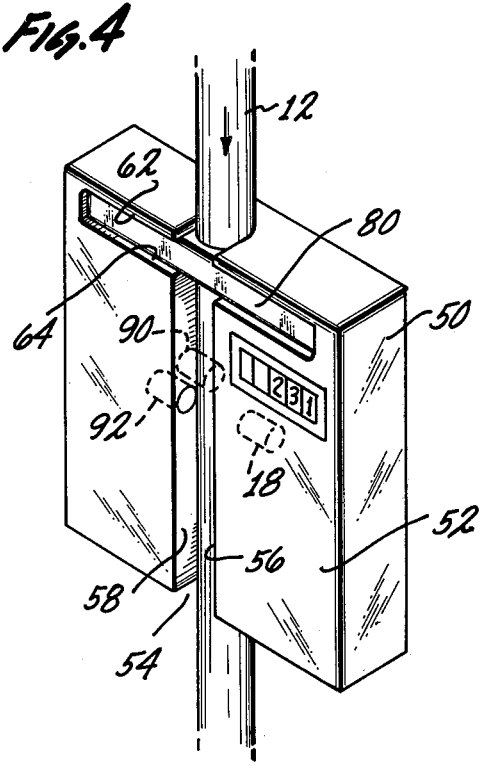
FIG. 4 is a perspective view, as seen from a position similar to that shown in FIG. 2, of a modified form of the rate meter.
Figure 5:
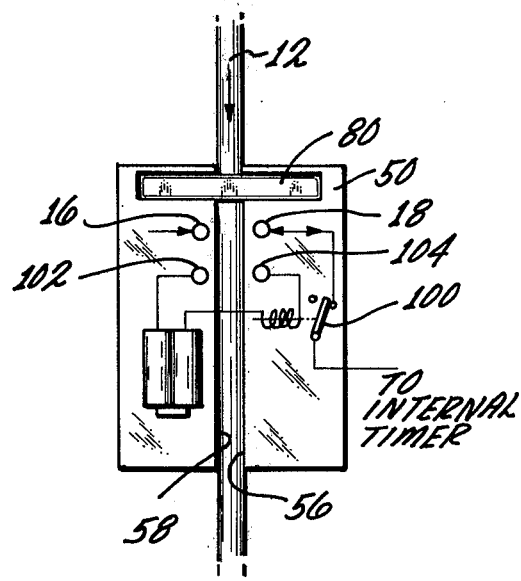
FIG. 5 is a schematic view of the rate meter shown in FIG. 2 and particularly illustrates circuitry for preventing the rate meter from operating until the rate meter has been properly disposed on the conduit.
Figure 6:
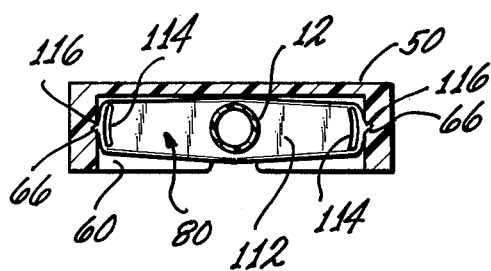
FIG. 6 is a sectional view of apparatus for holding the rate meter in fixed position on the conduit.

The rate meter may include more than one light source in the side wall 56. For example, a pair of light sources 90 and 92 (FIG. 4) may be disposed in the side wall 56 at horizontally spaced positions but at substantially the same vertical level. When two light sources 90 and 92 are used, both sources are disposed to direct light to the sensor 18.

The use of more than one light source provides certain advantages. For example, it tends to minimize problems which may result from fogging of the conduit. Such fogging may occur by vaporization of the fluid in the conduit and also by the condensation of minute particles of the resultant vapor on the walls of the conduit. It also provides more complete illumination of the drip chamber and eliminates the need for a complex optical system.

Means may be included in the rate meter to conserve energy. Conservation of energy is desirable to prolong the life of the batteries in the housing 50. Such energy-conserving means may include a manually operated switch 100 or it may include a light source 102 and a sensor 104 respectively disposed in the walls 56 and 58. The source 102 and the sensor 104 may be operative at low energy levels to produce a signal for operating a switch (not shown) to interrupt power to the rate meter when the rate meter is not disposed on the conduit 12. When the rate meter is disposed on the conduit 12, the conduit interrupts the light passing to the sensor 104 and causes the rate meter to become activated.

The coupling member 80 may be molded from a plastic material having resilient properties. The coupling member 80 may be in the form of a relatively thin cross bar 112 shaped to fit snugly in the horizontally disposed channel 60. The cross bar 112 may be provided with slots 114 near its outer ends to increase its resiliency at its outer ends. The slots may extend along substantially the full length from the front to the rear of the cross bar. The cross bar may also be provided with detents to engage the detents at the opposite ends of the horizontally disposed channel 60. When the detents in the channel 60 constitute recesses 66, the detents in the cross bar 112 may constitute fingers 116 for retention in the recesses. In this way, the housing 50 may be easily disposed on the cross bar for fixed retention on the cross bar but may be easily removed from the cross bar.

Although this application has been disclosed and illustrated with reference to particular applications, the principles involved are susceptible of numerous other applications which will be apparent to persons skilled in the art. The invention is, therefore, to be limited only as indicated by the scope of the appended claims.

We claim:

1. In combination for providing a visual display of the rate at which drops of fluid fall through a drip chamber,
    a housing having a size to be carried on the belt of a hospital attendant,
    sensing means disposed in the housing and responsive to the flow of the drops through the drip chamber for producing signals representing such flow,
    means disposed in the housing and responsive to the signals from the sensing means for initiating a timing interval in accordance with the fall of fluid drops through the drip chamber and for interrupting the timing interval upon the fall of the next drops of fluid through the drip chamber,
    means disposed in the housing for providing clock signals,
    means disposed in the housing for counting the clock signals during each timing interval,
    means disposed in the housing for generating the reciprocal of the count of the clock signals to provide an indication of the rate at which drops of fluid fall through the drip chamber, and
    means disposed in the housing and coupled to the drip-sensing means, the timing-interval means, the clock signal means, the counting means and the rate-indicating means for providing the energy for obtaining an operation of such means.

2. The combination set forth in claim 1, including,
    means for multiplying the reciprocal count by sixty (60) to obtain the rate per minute of the fall of the fluid drops.

3. In combination for providing a visual display of the rate at which drops of fluid fall through a drip chamber and for retention on the drip chamber during such visual display, a housing having a size to be carried in the pocket of a hospital attendant and to be supported on the drip chamber, sensing means disposed in the housing and responsive to the flow of the drops of fluid through the drip chamber for producing signals representing such flow, means responsive to successive signals from the sensing means for producing gating periods corresponding to the times between the production of the successive signals, means for providing clock signals at a particular frequency, means for determining the number of clock signals in each gating period, means disposed in the housing and responsive to the determination of the number of clock signals in each gating period for operating in accordance with such determination, to obtain an indication of the rate of fluid flow, means disposed in the housing and coupled to the sensing means, the means producing the gating periods, the clock signal means, the means determining the number of clock signals in each gating period and the rate-indicating means for providing the energy for operating such means, and means provided in the housing for cooperating with the drip chamber to obtain a detachable retention of the housing by the drip chamber.

4. The combination set forth in claim 3 wherein
the rate-indicating means includes means for generating the reciprocal of the number of clock signals in each gating period, and means for visually indicating the value of such reciprocal generation.

5. The combination set forth in claim 4 wherein
the rate-indicating means further includes means for multiplying the reciprocal generation by 60 to obtain an indication of the rate of the drops per minute.

6. In combination for providing a visual display of the rate at which drops of fluid flow through a drip chamber, a housing having a vertically disposed channel for receiving the drip chamber and having a horizontally disposed channel communicating with the vertically disposed channel and having first detent means in the horizontally disposed channel, coupling means supported by the drip chamber for disposition in the horizontally disposed channel of the housing and having second detent means for releasably cooperating with the first detent means to retain the housing on the coupling means, means included in the housing in facing relationship to the drip chamber, with the drip chamber disposed in the vertically disposed channel in the housing, for sensing the fall of drops of fluid through the drip chamber and for producing signals representing such flow, and means included in the housing and responsive to the signals representing the drops of fluid for producing a visual indication of the rate of fluid flow.

7. The combination set forth in claim 6, wherein,
the coupling means include resilient arms at its ends to facilitate the insertion of the coupling means into the horizontally disposed channel and the removal of the coupling means from the horizontally disposed channel and wherein the second detent means is disposed in such resilient arms to provide a coupling between the coupling means and the housing.

8. The combination set forth in claim 7, including,
means disposed in the housing for providing the power for operating the sensing means and the rate-indicating means.

9. The combination set forth in claim 6, wherein
the housing includes first and second walls which are disposed in spaced relationship to each other and which define the vertically disposed channel and which are adjacent the drip chamber when the drip chamber is disposed in the vertically disposed channel and wherein at least one light source is disposed in the first wall in facing relationship to the drip chamber and a sensor is disposed in the second wall in facing relationship to the drip chamber and wherein the housing includes a front wall and the rate-indicating means includes a visual display in the front wall.

10. In combination for use with a drip chamber and a cross bar, with detents at the ends of the cross bar, for providing a visual display of the rate at which drops of fluid fall through the drip chamber, a housing having walls defining an upper support shelf and a channel disposed horizontally below the support shelf and defining the support shelf and shaped to receive the drip chamber and a support wall defining the bottom of the horizontally disposed channel and having first and second vertically disposed walls facing each other and defining a vertically disposed channel, there being detents in the walls defining the horizontal boundaries of the horizontal channel for cooperating with the detents in the cross bar to retain the housing on the cross bar, the housing having dimensions to be carried in the pocket of a hospital attendant and to be supported by the drip chamber, means disposed in the first vertically disposed wall for providing at least one light source, means disposed in the second vertically disposed wall for defining a light sensor to produce signals in accordance with the light passing to the sensor, means disposed in the housing and responsive to the signals from the light sensor for operating upon such signals to provide an indication of the rate at which drops of fluid fall through the drip chamber, and means disposed in the housing and coupled to the light sensor, the light source and the rate-indicating means for providing energy to such means to obtain an operation of such means.

11. The combination set forth in claim 10 wherein
the housing includes a front panel and wherein the rate-indicating means comprises display means disposed in the front panel to display the rate at which the drops of fluid fall through the drip chamber.

12. The combination set forth in claim 11 wherein
the light source means, the light sensor means and the rate-indicating means and the energy-providing means are disposed in the housing to make the rate meter self-contained and wherein batteries are included in the housing as the energy-providing means to supply energy to the light source means, the light sensor means and the rate-indicating means.

13. The combination set forth in claim 12 wherein the detents in the cross bar constitute fingers extending outwardly from opposite ends of the cross bar and the detents in the housing constitute recesses for receiving the fingers.

14. The combination set forth in claim 10 wherein the light source means includes a pair of light sources disposed in the first vertically disposed wall at spaced positions for introducing light into the drip chamber and wherein the light sensor means is disposed in the second vertically disposed wall to receive the light from the pair of light source means.

15. The combination set forth in claim 12 wherein switch means are included on the housing for maintaining the light source means and the sensor means inoperative until the housing is disposed on the cross bar.

16. In combination for facilitating a visual display by a rate meter of the rate of fall of drops of fluid from a source to a patient,
   a drip chamber for guiding the drops of fluid to the patient,
   a cross bar fixedly disposed on the drip chamber for coupling to the rate meter, the cross bar being made from a resilient material and being provided with slots at its ends to enhance the resiliency of the cross bar, and
   fingers at the ends of the cross bars to function as detents for retaining the rate meter.

17. The combination set forth in claim 16 wherein the cross bar is provided with an aperture for receiving the drip chamber and wherein the slots extend along substantially the length of the cross bar at the ends of the cross bar.

18. The combination set forth in claim 17 wherein the rate meter includes a support shelf and a support wall spaced from each other to define a horizontally disposed channel and further includes recesses at the opposite ends of the channel and wherein the cross bar is constructed to be disposed in the channel and the fingers are constructed to be engaged in the recesses.

19. The combination set forth in claim 18 wherein the cross bar is sealed on the drip chamber.

20. In combination for providing a visual display of the rate at which drops of fluid fall through a drip chamber, where coupling means are included and are provided with detent means,
   a housing having a vertically disposed channel for receiving the drip chamber and having a horizontally disposed channel communicating with the vertically disposed channel and constructed to receive the coupling means, the housing having detent means in the horizontally disposed channel for cooperating with the detent means in the coupling means to retain the coupling means in the horizontally disposed channel,
   the housing being provided with a size to fit in the pocket of a hospital attendant and to be supported by the drip chamber,
   means included in the housing in facing relationship to the drip chamber, with the drip chamber disposed in the vertically disposed channel in the housing, for sensing the fall of drops of fluid through the drip chamber and for producing signals representing such fall,
   means included in the housing and responsive to the signals from the sensing means for determining the rate at which the drops of fluid fall through the drip chamber, and
   means included in the housing and responsive to the determinations of the rate of the fall of the drops of fluid for visually indicating such rate.

21. In combination for providing a visual display of the rate at which drops of fluid fall through a drip chamber, where coupling means are included and are provided with detent means,
   a housing having a vertically disposed channel for receiving the drip chamber and having a horizontally disposed channel communicating with the vertically disposed channel and constructed to receive the coupling means, the housing having detent means in the horizontally disposed channel for cooperating with the detent means in the coupling means to retain the coupling means in the horizontally disposed channel,
   means included in the housing in facing relationship to the drip chamber, with the drip chamber disposed in the vertically disposed channel in the housing, for sensing the fall of drops of fluid through the drip chamber and for producing signals representing such fall,
   means included in the housing and responsive to the signals from the sensing means for determining the rate at which the drops of fluid fall through the drip chamber, and
   means included in the housing and responsive to the determinations of the rate of the fall of drops of fluid for visually indicating such rate,
   the vertically disposed channel being defined by first and second side walls in the housing in facing relationship to each other and the sensing means including at least one light source in the first wall and a sensor in the second wall and the determining means being operative to determine the rate of fall of drops of fluid from a pair of signals representing successive drops through the drip chamber.

22. The combination set forth in claim 21 wherein the housing includes a front wall and the indicating means is disposed in the front wall and the determining means includes means for determining the time period between the production of successive pairs of signals by the sensing means and means for producing clock signals during each such time period and means for counting such clock signals during each such time period and means for operating upon such count to determining the rate of the fall of drops of fluid.

23. The combination set forth in claim 22 wherein the detent means in the horizontally disposed channel include recesses and wherein the determining means include means for inverting the count of the clock signals during each successive time period to obtain an indication of the rate of the fall of drops of fluid.

24. The combination set forth in claim 22 wherein the sensing means includes at least a pair of spaced light sources in the first wall and wherein the sensor is disposed to sense the light from the pair of spaced light sources.

* * * * *